United States Patent
Maeda et al.

Patent Number: 5,728,683
Date of Patent: Mar. 17, 1998

[54] EXTERNAL ESCINOL PREPARATION FOR SKIN

[75] Inventors: Kazuhisa Maeda; Rumiko Kaku; Yoshihiro Yokokawa; Minoru Fukuda, all of Yokohama, Japan

[73] Assignee: Shiseido Co., Ltd., Tokyo, Japan

[21] Appl. No.: 604,979

[22] PCT Filed: Jul. 7, 1995

[86] PCT No.: PCT/JP95/01360

§ 371 Date: Apr. 19, 1996

§ 102(e) Date: Apr. 19, 1996

[87] PCT Pub. No.: WO96/01618

PCT Pub. Date: Jan. 25, 1996

[30] Foreign Application Priority Data

Jul. 7, 1994 [JP] Japan ................................. 6-179544
Feb. 21, 1995 [JP] Japan ................................. 7-058149

[51] Int. Cl.$^6$ ................................. A01N 43/04; A61K 31/70
[52] U.S. Cl. ................................. 514/33; 514/33; 514/561; 424/62
[58] Field of Search ................................. 514/33, 25, 56; 424/62

[56] References Cited

U.S. PATENT DOCUMENTS

| | | | |
|---|---|---|---|
| 5,541,220 | 7/1996 | Ismail | 514/458 |
| 5,580,549 | 12/1996 | Fakuda et al. | 514/944 |

FOREIGN PATENT DOCUMENTS

| | | |
|---|---|---|
| 53-9328 | 2/1978 | Japan . |
| 62-81306 | 7/1985 | Japan . |
| 1-93519 | 2/1987 | Japan . |
| 63-8314 | 1/1988 | Japan . |
| 4-169515 | 6/1988 | Japan . |
| 2-117619 | 5/1990 | Japan . |
| 3-279317 | 12/1991 | Japan . |
| 07061998 | 3/1995 | Japan . |

OTHER PUBLICATIONS

Ogura, Suzuki, Tamada & Fujimoto Studies on the Anti-Inflammatory Action of Horse-Chestnut Saponin (1975).
Yoshikawa et al. Escins-Ia,Ib,IIa,IIb, and IIIa . . . Jun. 1994.
Mitsubishi Rayon Co. Ltd. Back Protection Screen, abstract Oct. 1987.
Shiseido Co.Ltd. External Agent for Skin, abstract Sep. 1986.
Shiseido Co.Ltd. Dyestuff Deposition Inhibitor, abstract Mar. 1995.
CA 114:181954, Omelkova et al. 1990.

*Primary Examiner*—Rebecca Cook
*Attorney, Agent, or Firm*—Ronald R. Snider

[57] ABSTRACT

An external preparation for skin comprising at least one member selected from the group consisting of escinol and its salts represented by the following constitutional formula (1):

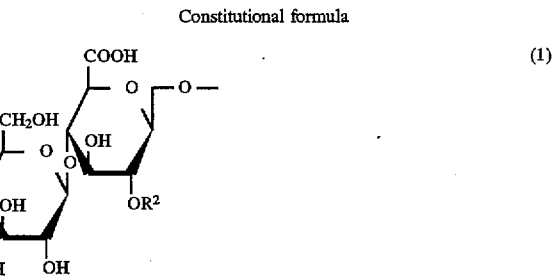

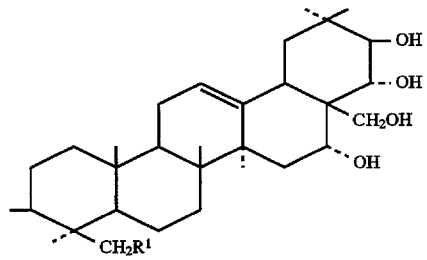

(wherein $R^1$ is hydrogen atom or hydroxyl group and $R^2$ is pyranose residue.)

Due to the effect of escinol which characterizes the present invention, the external preparation in accordance with the present invention is excellent in whitening effect and has a high safety.

15 Claims, No Drawings

EXTERNAL ESCINOL PREPARATION FOR SKIN

This is a 371 of PCT/JP95/01360 filed Jul. 7, 1995.

[TECHNICAL FIELD]

The present invention relates to an external preparation for skin and, more particularly, to an external preparation for skin which is excellent in whitening effect and has good usability and safety.

[BACKGROUND ART]

Aging phenomenon in skin which is exemplified by lines at corners of eyes and deposition of pigment such as spots and freckles appears earlier than that in other tissues and organs. It is often observed at an age as early as middle twenties. This is supposed to be because that the skin is at the outermost layer of an organism where it is likely to receive external stimulation (i.e., stress) such as ultraviolet rays, oxygen, and chemical substances.

The deposition of melanin pigment on the skin such as spots or freckles due to ultraviolet rays and stress occurs when pigment cells, which are melanin-producing cells, grow or the melanin-producing function within the pigment cell is accelerated. Recent studies have been elucidating that spots and freckles are generated when factors for activating the pigment cells within the skin increase in this manner due to the ultraviolet rays and stress.

Conventionally, in order to prevent these obstacles in the skin and to attain whitening effect, ascorbic acid and its derivatives have been widely used.

However, it is difficult for conventionally-used ascorbic acid and its derivatives to sufficiently exhibit the effect on preventing the deposition of pigment.

On the other hand, escinol is a kind of triterpenoid saponin formed when escin (i.e., a mixture of a plurality of kinds of saponin) in an extract of seeds of *Asculus hippocastanum* L is alkali-decomposed so as to eliminate its acyl group. It does not exist in the extract of seeds of *Asculus hippocastanum* L and in escin.

Since the extract of seeds of *Asculus hippocastanum* L has an anti-inflammatory effect, it has been known to be compounded in cosmetic preparations in order to prevent the skin from flushing (Japanese Unexamined Patent Publication Sho No. 53-9328, Japanese Unexamined Patent Publication Sho No. 62-81306, and Japanese Unexamined Patent Publication Hei No. 2-117619). Also, it has been clarified that escin has an anti-inflammatory effect as an effective ingredient in the extract of seeds of *Asculus hippocastanum* L (Oyo Yakuri 9:883, 1975).

Further, the inventors have elucidated that escin has an effect on resistance to the deposition of pigment, i.e., whitening effect (Japanese Patent Application Hei No. 5-246161). However, it has not yet been known at all that escinol has a whitening effect.

[DISCLOSURE OF INVENTION]

In view of the above-mentioned problem of the prior art, the object of the present invention is to provide an external preparation for skin which is excellent in whitening effect, by which the deposition of pigment is suppressed directly and effectively, and has good usability and safety.

As the result of diligent studies of the inventors for attaining the above-mentioned object, it has been found that escinol and its salts have an excellent whitening effect and are excellent in usability and safety. Accordingly, the present invention has been achieved.

Namely, the present invention provides an external preparation for skin comprising one or more than two members selected from the group consisting of escinol and its salts.

In the following, the constitution of the present invention will be explained in detail.

Escinol and its salts in the present invention have an effect on suppressing the production and action of factors for activating pigment cells in the skin. As a result, production of melanin in the pigment cells and abnormal growth of the pigment cells are suppressed.

Escinol and its salts, which are effective ingredients in the external preparation for skin in accordance with the present invention, are a compound represented by the following constitutional formula (1) (escinol) and its salts and have been known to have a cytotoxicity much lower than that of escin (Folia Histchemica et Cytchemica 16:69, 1978).

Constitutional formula

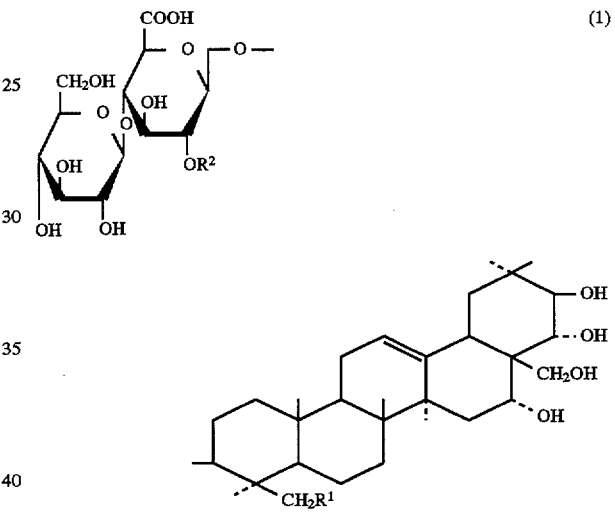

(wherein $R^1$ is hydrogen atom or hydroxyl group and $R^2$ is pyranose residue)

However, its whitening effect has not yet been known at all. Further, no external preparation for skin comprising escinol or its salts has been known at all.

Such escinol and its salts can be obtained when an extract from a plant such as seeds of *Asculus hippocastanum* L or escin is alkali-decomposed. For example, escin is dissolved in sodium methylate/methanol solution, heat-refluxed, and then allowed to cool to room temperature. After being neutralized by a strongly acidic resin, the resulting mixture is filtered to remove the resin and then the filtrate is concentrated. Thus concentrated filtrate is fractioned by gel chromatography such as that performed on Wako Gel C-200 column and then refined. Alternatively, it is recrystallized after being heat-refluxed. Thus obtained escinol contains at least one kind of the compound represented by the above-mentioned constitutional formula (1).

As escinol in the above-mentioned constitutional formula (1), one in which $R^1$ is hydroxyl group and $R^2$ is β-D-glucopyranose, one in which $R^1$ is hydroxyl group and $R^2$ is β-D-xylopyronose, and one in which $R^1$ is hydrogen atom and $R^2$ is β-D-galactopyranose have been confirmed [M. YOSHIKAWA et al., Chem. Pharm. Bull. 42 (6) 1357–1359 (1994)].

Examples of salts of escinol include alkaline metal salts such as sodium salt and potassium salt; alkaline amino acids; and alkanol amines; and the like and their esters or the like. Their specific examples include sodium salt of escinol, potassium salt of escinol, ammonium salt of escinol, and the like.

While the compounding amount of escinol and its salts may be selected appropriately according to their form of use, purpose of use, method of use, type of formulation, and the like, they are compounded usually at 0.001–20.0% by weight and preferably at 0.01–5.0% by weight with respect to the whole amount of the composition. When compounded in a cosmetic preparation for skin, it is desirable for them to be used at not less than 0.1% by weight with respect to the whole amount of the composition.

When escinol and its salts are used together with tranexamic acid and/or arbutin, their whitening effect is further intensified. The whitening effect of tranexamic acid and arbutin used here has been known (Japanese Unexamined Patent Publication Hei No. 1-93519 and Japanese Patent Publication Hei No. 4-15764). While the compounding ratio of tranexamic acid and/or arbutin in this case may be selected appropriately, they are used usually at 0.001–20.0% by weight and preferably at 0.01–7.0% by weight with respect to the whole amount of the composition. These ingredients may be used separately as well as in combination of two or more. Escinol and its salts which are effective ingredients of the external preparation for skin in accordance with the present invention do not yield any unfavorable influence locally or totally.

Further, in addition to the above-mentioned essential ingredients, the external preparation for skin in accordance with the present invention may be used together with polysaccharides, cholesterols, placenta extract, extracts of plants such as licorice, glycyrrhizic acid and its derivatives, glycyrrhetic acid and its derivatives, tocopherol and its derivatives, ascorbic acid and its derivatives, kojic acid and its derivatives, hydroquinones, flavonoid, retinol, hinokitiol, indomethacin, antioxidants, for example, butylhydroxy toluene and the like, and ultraviolet-absorbing agents.

According to normal techniques, the external preparation for skin in accordance with the present invention can be formed into various formulas of cosmetic preparations and medical preparations with other ingredients such as excipient, oil, surfactant, antiseptic, humectant, perfume, water, alcohol, thickener, coloring material, and the like which are usually used may be appropriately compounded therein when necessary, in addition to the above-mentioned indispensable ingredients. Also, as an internal medicine, it may be formed into various formulas of tablet, granule, powder, syrup, drink, and the like.

[BEST MODE FOR CARRING OUT THE INVENTION]

In the following, the present invention will be further explained with reference to its examples. The present invention, however, is not restricted by the following examples.

Escinol used in this embodiment contains at least one kind of the compound represented by the constitutional formula (1) resulting from an alkali decomposition of escin contained in the extract of seeds of *Asculus hippocastanum* L and can be obtained by the following method.

Namely, escin extracted from seeds of *Asculus hippocastanum* L is dissolved in sodium methylate/methanol solution, heat-refluxed, and then allowed to cool to room temperature. After being neutralized by a strongly acidic resin, the resulting mixture is filtered to remove the resin and then the filtrate is concentrated. Thus concentrated filtrate is fractioned by gel chromatography such as that on Wako Gel C-200 column and then refined. Alternatively, it is recrystallized after being heat-refluxed.

Thus obtained escinol contains one or more than two kinds of the compound represented by the constitutional formula (1).

Prior to the examples, the effectiveness of the present invention will be indicated with reference to test examples concerning effectiveness of the effective ingredients in the present invention. Namely, according to the formulas shown in Table 1, lotion samples were prepared and then their whitening effect was examined.

[TEST METHOD]

A panel of 70 females whose ages ranging from 29 to 49 having spots, freckles, and the like on their faces was divided into 14 groups each comprising 5 members. To the faces of members of each group, each lotion sample containing the indicated ingredients had been applied once a day for 3 months and its whitening effect after use was judged on the basis of the following judgment standard.

[JUDGMENT STANDARD]

Remarkably effective: pigment deposition has become inconspicuous

Effective: pigment deposition has become substantially faint

Fairly effective: pigment deposition has become somewhat faint

No effect: pigment deposition has not changed

[JUDGMENT]

A: where the ratio of remarkably effective, effective, and fairly effective in the examinees is not less than 80%

B: where the ratio of remarkably effective, effective, and fairly effective in the examinees is 65–80%

C: where the ratio of remarkably effective, effective, and fairly effective in the examinees is 50–65%

D: where the ratio of remarkably effective, effective, and fairly effective in the examinees is less than 50%

[RESULTS]

The results are shown in Table 1 together with the formulas.

TABLE 1

| Ingredient | 1 | 2 | 3 | 4 | 5 | 6 | 7 | 8 |
|---|---|---|---|---|---|---|---|---|
| Escinol | 0.0001 | 0.001 | 0.01 | 0.1 | 1.0 | 5.0 | 10.0 | 20.0 |
| Ethanol | 25 | 25 | 25 | 25 | 25 | 25 | 25 | 25 |

TABLE 1-continued

| Ingredient | 1 | 2 | 3 | 4 | 5 | 6 | 7 | 8 |
|---|---|---|---|---|---|---|---|---|
| Polyoxyethylene oleyl alcohol | 0.2 | 0.2 | 0.2 | 0.2 | 0.2 | 0.2 | 0.2 | 0.2 |
| Glycerin | 5.0 | 5.0 | 5.0 | 5.0 | 5.0 | 5.0 | 5.0 | 5.0 |
| Purified water | balance | balance | balance | balance | balance | balance | balance | balance |
| Whitening effect | D | C | B | B | A | A | A | A |

In view of these results, it is understood that the external preparation for skin in accordance with the present invention is excellent in the whitening effect. The whitening effect began to be observed when escinol was about 0.001% and became remarkable when escinol was not less than 0.01%. However, large improvement in effect could not be observed even when 5.0% or more of escinol was compounded. When escinol exceeded 10% by weight, there were cases where the solubility or the like was problematic.

In the following, compounding of tranexamic acid, arbutin, and ascorbic acid together with escinol will be studied.

The results are shown in Table 2 together with the formulas.

TABLE 2

| Ingredient | 9 | 10 | 11 | Comp. Ex. 1 | Comp. Ex. 2 | Comp. Ex. 3 |
|---|---|---|---|---|---|---|
| Escinol | 0.1 | 0.05 | 0.05 | — | — | — |
| Tranexamic acid | — | 0.5 | — | 1.0 | — | — |
| Arbutin | — | — | 0.5 | — | 1.0 | — |
| Ascorbic acid | — | — | — | — | — | 3.0 |
| Ethanol | 25 | 25 | 25 | 25 | 25 | 25 |
| Polyoxyethylene oleyl alcohol | 0.2 | 0.2 | 0.2 | 0.2 | 0.2 | 0.2 |
| Glycerin | 5.0 | 5.0 | 5.0 | 5.0 | 5.0 | 5.0 |
| Purified water | balance | balance | balance | balance | balance | balance |
| Whitening effect | B | A | A | C | C | C |

As clearly indicated by the above results, the evaluation of whitening effect was B when 0.1% of escinol was compounded alone, whereas the whitening effect was C when each of tranexamic acid, arbutin, or ascorbic acid was compounded alone. On the other hand, the whitening effect was A when escinol was compounded together with tranexamic acid or arbutin, thereby a synergistic effect was observed therebetween.

In the following, the present invention will be further explained with reference to examples. The present invention, however, is not restricted thereby. The compounding amounts refer to % by weight unless otherwise indicated.

EXAMPLE 1

Vanishing Cream

| | |
|---|---|
| Stearic acid | 5.0 |
| Stearyl alcohol | 4.0 |
| Butyl alcohol stearate | 8.0 |
| Glycerin monostearate | 2.0 |
| Escinol | 0.5 |
| Propylene glycol | 10.0 |
| Glycerin | 4.0 |
| Caustic potash | 0.2 |
| Antiseptic/antioxidant | q.s. |
| Perfume | q.s. |
| Ion-exchanged water | balance |

(Process Of Manufacture)

Propylene glycol, caustic potash, and escinol are added to and dissolved in ion-exchanged water. The resulting solution is heated and maintained at 70° C. (thereby forming an aqueous phase). The other ingredients are mixed together, melted by heating, and maintained at 70° C. (thereby forming an oil phase). The oil phase is gradually added to the aqueous phase. After the whole oil phase is added, the resulting mixture is maintained at the temperature at that time to effect a reaction. Thereafter, it is uniformly emulsified by a homomixer and then cooled to 30° C. while being stirred well.

EXAMPLE 2

Neutral Cream

| | |
|---|---|
| Stearyl alcohol | 7.0 |
| Stearic acid | 2.0 |
| Lanolin | 2.0 |
| Squalane | 5.0 |
| 2-octyldodecyl alcohol | 6.0 |
| Polyoxyethylene (25 mol) cetyl alcohol ether | 3.0 |
| Glycerin monostearate | 2.0 |
| Arbutin | 3.0 |
| Sodium salt of escinol | 1.0 |
| Antiseptic/antioxidant | q.s. |
| Ion-exchanged water | balance |

7

(Process Of Manufacture)

Arbutin and sodium salt of escinol are added to ion-exchanged water. The resulting mixture is heated and maintained at 70° C. (thereby forming an aqueous phase). The other ingredients are mixed together, melted by heating, and maintained at 70° C. (thereby forming an oil phase). The oil phase is added to the aqueous phase and then pre-emulsification is effected. Thereafter, the resulting mixture is uniformly emulsified by a homomixer and then cooled to 30° C. while being stirred well.

EXAMPLE 3

Cold Cream

| | |
|---|---|
| Solid paraffin | 5.0 |
| Beeswax | 10.0 |
| Liquid paraffin | 41.0 |
| Glycerin monostearate | 2.0 |
| Polyoxyethylene (20 mol) sorbitan monolaurate | 2.0 |
| Tranexamic acid | 1.0 |
| Escinol | 2.0 |
| Butylhydroxy toluene | 0.4 |
| Soap powder | 0.1 |
| Borax | 0.2 |
| Ion-exchanged water | balance |
| Perfume | q.s. |
| Antiseptic | q.s. |

(Process Of Manufacture)

Soap powder, borax, tranexamic acid, and escinol are added to and dissolved by heating in ion-exchanged water. The resulting mixture is maintained at 70° C. (thereby forming an aqueous phase). The other ingredients are mixed together, melted by heating, and maintained at 70° C. (thereby forming an oil phase). While being stirred, the oil phase is gradually added to the aqueous phase to effect a reaction. After the reaction is completed, the resulting mixture is uniformly emulsified by a homomixer. After the emulsification, the mixture is cooled to 30° C. while being stirred well.

EXAMPLE 4

Milky Lotion

| | |
|---|---|
| Stearic acid | 2.5 |
| Cetyl alcohol | 1.5 |
| Liquid paraffin | 10.0 |
| Polyoxyethylene (10 mol) mono-oleate | 2.0 |
| Polyethylene glycol 1500 | 3.0 |
| Triethanolamine | 1.0 |
| Potassium salt of escinol | 0.1 |
| α-tocopherol | 0.1 |
| Ion-exchanged water | balance |
| Perfume | q.s. |
| Antiseptic | q.s. |

(Process Of Manufacture)

Polyethylene glycol, triethanolamine, and potassium salt of escinol are added to and dissolved by heating in ion-exchanged water. The resulting mixture is maintained at 70° C. (thereby forming an aqueous phase). The other ingredients are mixed together, melted by heating, and maintained at 70° C. (thereby forming an oil phase). The oil phase is added to the aqueous phase and then pre-emulsification is effected. Thereafter, the resulting mixture is uniformly emulsified by a homomixer and then cooled to 30° C. while being stirred well.

8

EXAMPLE 5

Milky Lotion

| | |
|---|---|
| Microcrystalline wax | 1.0 |
| Cetanol | 1.0 |
| Beeswax | 2.0 |
| Lanolin | 1.5 |
| Liquid paraffin | 3.0 |
| Glycerin | 2.0 |
| Sorbitan sesquioleate | 4.0 |
| Polyoxyethylene (20 mol) sorbitan mono-oleate | 1.0 |
| Propylene glycol | 5.0 |
| Tranexamic acid | 5.0 |
| Escinol | 0.5 |
| Ion-exchanged water | balance |
| Perfume | q.s. |
| Antiseptic/antioxidant | q.s. |

(Process Of Manufacture)

Propylene glycol, tranexamic acid, and escinol are added to and dissolved by heating in ion-exchanged water. The resulting mixture is maintained at 70° C. (thereby forming an aqueous phase). The other ingredients are mixed together, melted by heating, and maintained at 70° C. (thereby forming an oil phase). The oil phase is added to the aqueous phase and then pre-emulsification is effected. Thereafter, the resulting mixture is uniformly emulsified by a homomixer and then cooled to 30° C. while being stirred well.

EXAMPLE 6

Lotion

| | |
|---|---|
| (Alcohol Phase) | |
| 95% Ethyl alcohol | 10.0 |
| Polyoxyethylene hardened castor oil | 2.0 |
| Propylene glycol | 4.0 |
| Oleyl alcohol | 0.1 |
| Lecithin | 2.5 |
| (Aqueous Phase) | |
| Glycerin | 0.8 |
| Ammonium salt of escinol | 0.2 |
| Ion-exchanged water | balance |
| Ultraviolet-absorbing agent | q.s. |

(Process Of Manufacture)

The aqueous phase and alcohol phase are prepared and then solubilized.

EXAMPLE 7

Peel-Off Type Pack

| | |
|---|---|
| (Alcohol Phase) | |
| 95% Ethanol | 10.0 |
| Polyoxyethylene (15 mol) oleyl alcohol ether | 2.0 |
| Escinol | 5.0 |
| Antiseptic | q.s. |
| Perfume | q.s. |
| (Aqueous Phase) | |
| Polyvinyl alcohol | 12.0 |
| Glycerin | 3.0 |
| Polyethylene glycol 1500 | 1.0 |
| Tranexamic acid | 3.0 |
| Ion-exchanged water | balance |

(Process Of Manufacture)

The aqueous phase is prepared at 80° C. and then cooled to 50° C. The alcohol phase is prepared at room temperature and then added to the aqueous phase. Then, the resulting mixture is uniformly mixed and left for cooling.

As explained in the foregoing, due to the effect of escinol which characterizes the present invention, the external preparation in accordance with the present invention is excellent in whitening effect and prevents spots and freckles from being generated in the skin, thereby rendering a smooth and wet feel to the skin while maintaining a high safety.

Also, when escinol is used together with tranexamic acid or arbutin, the above-mentioned whitening effect is synergistically improved.

We claim:

1. An external preparation for skin comprising:
   (a) at least one member selected from the group consisting of escinol and a cosmetically or pharmaceutically acceptable salt of escinol represented by the following constitutional formula:

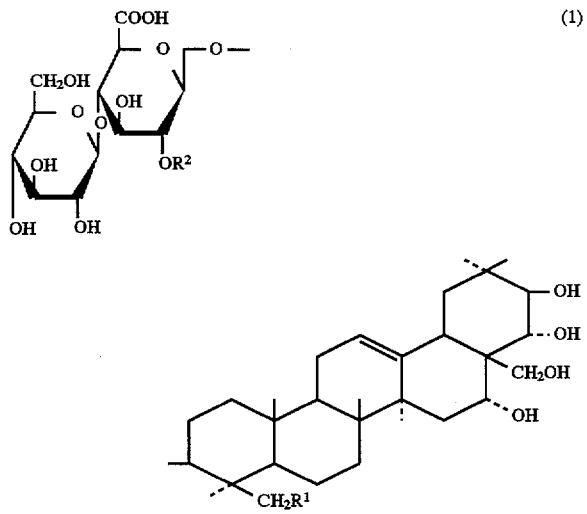

wherein $R^1$ is hydrogen atom or hydroxyl group and $R^2$ is selected from the group consisting of β-D-glucopyranose, β-D-xylopyranose and β-D-galactopyranose, and
   (b) a cosmetically or pharmaceutically acceptable carrier for application to the skin.

2. An external preparation for skin according to claim 1, in which the member selected from the group consisting of escinol and a cosmetically or pharmaceutically acceptable salt of escinol is compounded in an amount of 0.01%–5.0% by weight of the external preparation.

3. An external preparation for skin according to claim 1, further comprising tranexamic acid and/or arbutin.

4. An external preparation for skin according to claim 3, in which said tranexamic acid and/or arbutin is compounded in an amount of 0.01–7.0% by weight of the external preparation.

5. The external preparation for skin of claim 1, wherein said at least one member is selected from the group consisting of a sodium salt of escinol, a potassium salt of escinol and an ammonium salt of escinol.

6. The external preparation for skin of claim 1, wherein said member comprises 0.01–5.0% by weight of said preparation.

7. The external preparation of claim 1, wherein said member comprises not less than 0.1% by weight of said preparation.

8. The external preparation for skin of claim 1, comprising 0.001–20.0% tranexamic acid and/or arbutin by weight of said preparation.

9. The external preparation for skin of claim 1, further comprising at least one member selected from the group consisting of a polysaccharide, a cholesterol, placenta extract, extract of licorice, glycyrrhizic acid, glycyrrhetic acid, tocopherol, ascorbic acid, kojic acid, a hydroquinone, flavonoid, retinol, hinokitiol, indomethacin, an antioxidant and an ultraviolet-absorbing agent.

10. The external preparation for skin of claim 1, further comprising at least one member selected from the group consisting of an excipient, oil, surfactant, antiseptic, humectant, perfume, water, alcohol, thickener and coloring material.

11. A method, comprising:
   forming an external preparation for skin comprising at least one member selected from the group consisting of escinol and a cosmetically or pharmaceutically acceptable salt of escinol represented by the following formula:

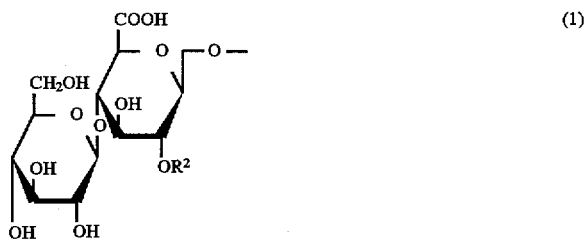

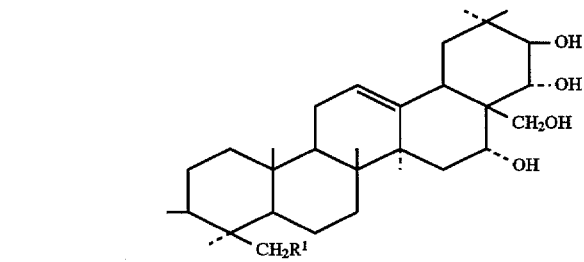

wherein $R^1$ is hydrogen atom or hydroxyl group and $R^2$ is selected from the group consisting of β-D-glucopyranose, β-D-xylopyranose and β-D-galactopyranose; and applying said preparation to whiten the skin.

12. The method of claim 11, wherein said preparation for skin comprises 0.001–5.0% by weight of said member.

13. The method of claim 11, wherein said preparation for skin further comprises tranexamic acid and/or arbutin.

14. The method of claim 12, wherein said preparation for skin further comprises tranexamic acid and/or arbutin.

15. The method of claim 11, wherein said preparation for skin further comprises 0.01–7.0% by weight tranexamic acid and/or arbutin.

* * * * *